United States Patent [19]

Bodor

[11] 4,140,796
[45] Feb. 20, 1979

[54] LABILE QUATERNARY AMMONIUM SALTS USEFUL IN BINDING BILE ACIDS IN WARM-BLOODED ANIMALS

[75] Inventor: Nicolae S. Bodor, Lawrence, Kans.

[73] Assignee: INTERx Research Corporation, Lawrence, Kans.

[21] Appl. No.: 809,850

[22] Filed: Jun. 24, 1977

Related U.S. Application Data

[62] Division of Ser. No. 691,781, Jun. 1, 1976, Pat. No. 4,046,899.

[51] Int. Cl.$^2$ .................. A61K 31/23; A61K 31/22; A61K 31/235; A61K 31/24
[52] U.S. Cl. .................. 424/312; 424/238; 424/308; 424/309; 424/311; 424/313; 424/317; 424/318
[58] Field of Search ............... 424/312, 311, 313, 308, 424/309, 317, 318, 238

[56] References Cited

FOREIGN PATENT DOCUMENTS 7288M 11/1969 France ........................... 424/312
7768M 3/1970 France ........................... 424/312

Primary Examiner—Frederick E. Waddell
Attorney, Agent, or Firm—Bacon & Thomas

[57] ABSTRACT

Free and conjugated bile acids are effectively bound in warm-blooded animals by administering thereto, a therapeutically effective bile acid binding amount of a quaternary ammonium compound having the formula:

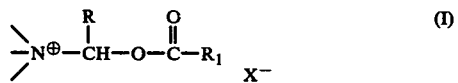

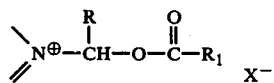

wherein

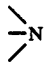

represents a tertiary open chain or cyclic aliphatic amine; wherein

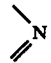

represents an unsaturated amine; wherein R represents a member selected from the group consisting of a hydrogen atom, a $C_1$-$C_{20}$ open chain or cyclo alkyl group, a $C_1$-$C_{20}$ alkoxy-alkyl group, a $C_1$-$C_{20}$ alkanoyloxyalkyl group, a $C_1$-$C_{20}$ haloalkyl group, a $C_1$-$C_{20}$ carboxyalkyl group, an aryl group, and a substituted aryl group, whose substituents are selected from the group consisting of a halogen atom, an O—$C_1$-$C_4$ alkyl group, an O—$C_1$-$C_8$ alkanoyl group, a nitro group, a carboxyl group, and a carboethoxy group; wherein $R_1$, which may be the same or different, represents any member defined by R above with the proviso that R cannot be a hydrogen atom, a

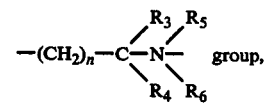

wherein $R_3$, $R_4$, $R_5$ and $R_6$ are each selected from the group consisting of a hydrogen atom, a methyl group or an ethyl group, a $C_0$-$C_{22}$ straight or branched

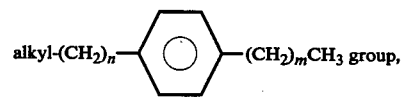

wherein n in each occurrence and m repesent an integer of from 0 to 22, an

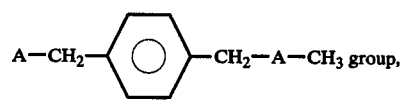

wherein A represents a $C_0$-$C_{22}$ straight or branched alkyl group as above or a —$(CH_2CH_2O)_p$— group, wherein the p represents an integer of from 0 to 22, and the residue of any naturally occurring bile acid or synthetic derivative thereof; and wherein $X^-$ represents a halogen atom or any other organic or inorganic monovalent anion are disclosed.

These compounds are relatively nontoxic and substantially bind bile acids in warm-blooded animals and thus reduce the ulcerogenic symptoms exhibited by those characterized as being ulcer-prone.

12 Claims, No Drawings

LABILE QUATERNARY AMMONIUM SALTS USEFUL IN BINDING BILE ACIDS IN WARM-BLOODED ANIMALS

CROSS-REFERENCE TO RELATED APPLICATIONS

This is a division of application Ser. No. 691,781, filed June 1, 1976, now U.S. Pat. No. 4,046,899, which in turn includes, in part, subject matter covered by co-pending applications, Ser. No. 482,513, filed June 24, 1974, now U.S. Pat. No. 3,998,815, and Ser. No. 615,519, filed Sept. 22, 1975, now U.S. Pat. No. 3,989,711, both in the name of the present inventor.

BACKGROUND OF THE INVENTION

1. FIELD OF THE INVENTION

The present invention relates to a method for binding free and conjugated bile acids in warm-blooded animals, e.g. humans, and more particularly, to a method for compensating for the propensity of warm-blooded animals to generate deleterious amounts of free and conjugated bile acids present in the stomach thereof as a result of duodenogastric regurgitation.

As used herein, the term "bile acids," unless otherwise indicated, always refers to free and conjugated bile acids.

2. DESCRIPTION OF THE PRIOR ART

Because it is thought that the gastric ulcer, and by gastric ulcer is meant an ulcer located in the stomach as opposed to other portions of the gastrointestinal tract, is caused primarily by the action of ulcerogenic factors such as hydrochloric acid and pepsin which disturb the mucous membrane forming the inner lining of the stomach, conventional pharmaco-therapeutico efforts aimed at the treatment of gastric ulcers have heretofore concentrated on controlling the action of hydrochloric acid and pepsin. Specifically, prior known methods for treating the gastric ulcer have been essentially directed toward the inhibition of gastrointestinal motility and secretion, the blocking of spasm and the neutralization of counteraction of hydrochloric acid in the gastric juice. Additionally, there further exists one school of thought contending that the gastric ulcer is caused by abnormal action of the central nervous system, and accordingly, treatment by means of various sedatives and/or tranquilizers has been proposed; however, there is virtual concensus that hyperacidity and particularly, hyperchlorohydria, i.e., hypersecretion of hydrochloric acid in the stomach, plus the presence of gastric pepsin are primarily responsible for the formation of the gastric ulcer.

Normally, the mucosal tissues of the stomach are protected by a film of mucin, the mucopolysaccharide secreted by the gastric mucosa. It has been theorized that this agent disturbs the mucous membrane of the stomach, thereby giving rise to the formation of ulcers. Accordingly, in the past, the proposed methods of treating the condition known as the gastric ulcer has primarily focused totally on counterbalancing the effect of excess hydrochloric acid together with other mineral acids and pepsin. Those modes of treatment which have been previously employed can be generally classified as follows:

(1) Application of antacid agents for the purpose of neutralizing excess hydrochloric acid, such agents including conventional inorganic basic salts, colloidal neutralizing agents, anion exchange resin, amino acids, carboxymethylcellulose, etc.;

(2) Application of anticholinergic agents;

(3) The use of absorbents and adsorbents; and (4) Introduction of agents to protect the mucous membrane of the stomach, per se.

In accordance with the present invention, an entirely novel approach to the treatment of gastric ulcers in warm-blooded animals is provided, in view of the recent evidence[1] that hyperchlohydria may, in fact, not be the primary causative agent of gastric ulcers. Apparently, it now appears that the reflux of duodenal contents, and especially bile, is an important etiologic factor in the formation of gastric ulcers. It has been determined that the stomach of a patient with a gastric ulcer contains bile more frequently and at higher concentrations than that which is found in the stomach of a normal subject. In an effort to explain this phenomenon, studies have shown that in normal subjects, the pylorus functions as a sphincter which has the capacity to prevent retrograde movement of duodeno contents into the stomach. For example, the human pylorus is associated with a zone of high pressure that relaxes with antral peristalsis, contracts with endogenous or exogenous hormonal stimulation, and generally regulates the regurgitation of duodenal contents into the stomach. It appears, therefore, that the failure or malfunction of the pylorus to function in its known capacity as an effective sphincter in certain individuals, gives rise to the elevated gastric bile acid levels in the stomach, and accordingly, renders such individual prone to gastric ulcers.

[1]. Fisher, et al, *The New England Journal of Medicine*, 288, No. 6, pp. 273-276 (Feb. 8, 1973).

The present invention provides a method, entirely novel in its approach to the treatment of the ulcer condition, which method is directed toward counteracting the elevated levels of gastric bile acids caused by the aforementioned pyloric incompetence.

SUMMARY OF THE INVENTION

Accordingly, it is one object of the present invention to effectively bind bile acids in the stomach of a warm-blooded animal characterized as ulcer-prone.

It is another object of the present invention to provide a method for achieving the foregoing which is highly effective and yet, extremely simple to administer.

Finally, it is another object of the present invention to effectively bind bile acids in the stomach of warm-blooded animals, characterized as being ulcer-prone, with compounds which are therapeutically effective, and yet, innocuous from the standpoint of toxicity and residual side effects.

All the foregoing objects are satisfied by administering to such warm-blooded animals, characterized as being ulcer-prone, a therapeutically effective bile acid binding amount of a compound having the formula:

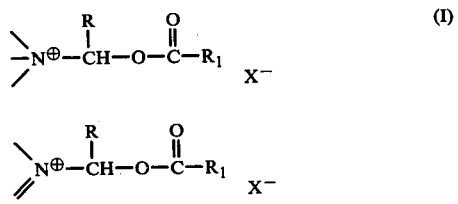

wherein

represents a tertiary open chain or cyclic aliphatic amine; wherein

represents an unsaturated amine; wherein R represents a member selected from the group consisting of a hydrogen atom, a $C_1$-$C_{20}$ open chain or cyclo alkyl group, a $C_1$-$C_{20}$ alkoxyalkyl group, a $C_1$-$C_{20}$ alkanoyloxyalkyl group, a $C_1$-$C_{20}$ haloalkyl group, a $C_1$-$C_{20}$ carboxyalkyl group, an aryl group, and a substituted aryl group, whose substituents are selected from the group consisting of a halogen atom, an O—$C_1$-$C_4$ alkyl group, an O—$C_1$-$C_8$ alkanoyl group, a nitro group, a carboxyl group, and a carboethoxy group; wherein $R_1$, which may be the same or different, represents any member defined by R above with the proviso that R cannot be a hydrogen atom, a

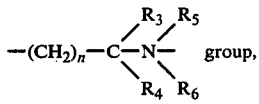

wherein $R_3$, $R_4$, $R_5$ and $R_6$ are each selected from the group consisting of a hydrogen atom, a methyl group or an ethyl group, a $C_0$-$C_{22}$ straight or branched

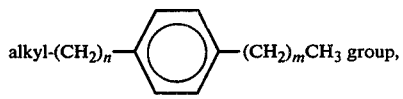

wherein n in each occurrence and m represent an integer of from 0 to 22, an

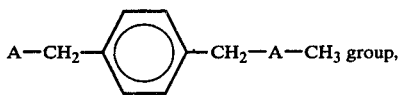

wherein A represents a $C_0$-$C_{22}$ straight or branched alkyl group as above or a —$(CH_2CH_2O)_p$ group, wherein the p represents an integer of from 0 to 22, and the residue of any naturally occurring bile acid or synthetic derivative thereof; and wherein $X^-$ represents a halogen atom or any other organic or inorganic monovalent anion.

The compounds described above with reference to generic formula (I) and their process of preparation, are amply described in applicant's co-pending applications, Ser. No. 482,513, filed June 24, 1974, now U.S. Pat. No. 3,998,815, and Ser. No. 615,519, filed Sept. 22, 1975, now U.S. Pat. No. 3,989,711. The subject matter of these applications, in their entirety, is incorporated herein by reference.

With regard to generic formula (I), reference to "aryl" denotes a phenyl or naphthyl group; reference to "halo" and "halogen" in each occurrence denotes any suitable member of the halogen series, e.g., chlorine, bromine or iodine; and reference to "alkanoyl" in the expression alkanoyl and alkanoyloxyalkyl denotes any convenient alkanoyl group such as a formyl group, an acetyl group, a propionyl group, a benzoyl group, etc. It is further noted that the term "substituted" insofar as "substituted aryl" is concerned refers to the fact that the aryl function may be substituted with any one or more of those substituents specifically defined herein.

As used in this application, the term "unsaturated amine" denotes N-heterocyclic unsaturated systems having 3–10 members in the ring, and substituted derivatives thereof where the unsaturation corresponds to the maximum number of noncumulative double bonds, provided that the nitrogen atom contains no hydrogen atom as a substituent. The following examples will sufficiently illustrate the scope of the above term:

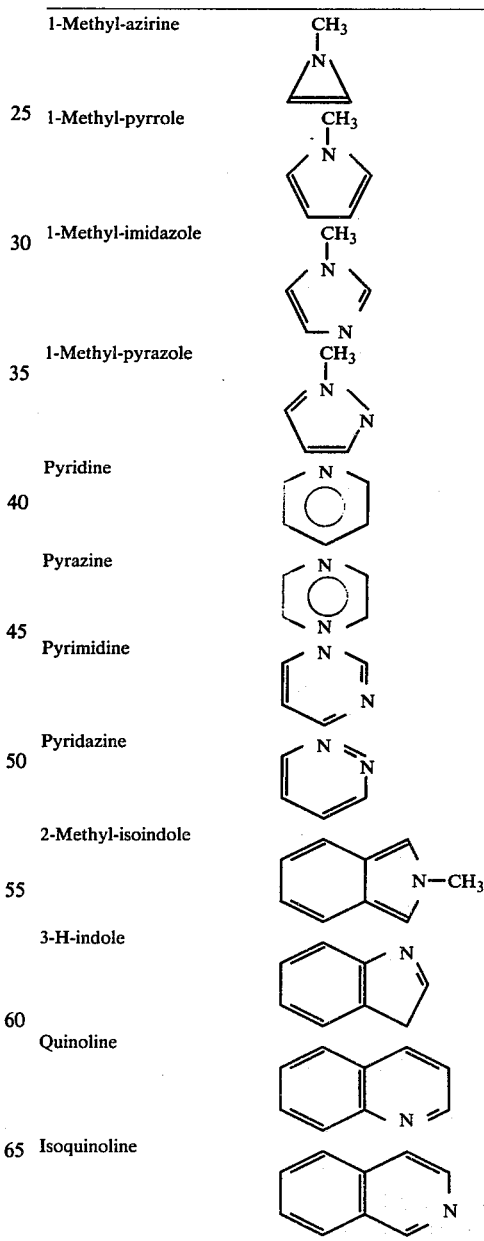

-continued

Phtalazine 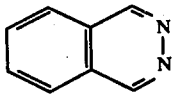

Quinoxiline 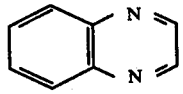

Quinazidine 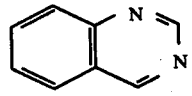

Phenazine 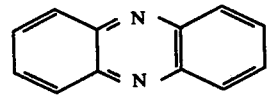

Isothiazole 

10-Methyl-phenothiazine 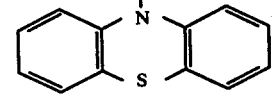

Isoxazole 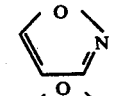

Furazan 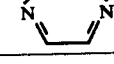

Insofar as the anion "X" is concerned, the term "organic or inorganic monovalent equivalent anion," denotes other equivalent anions such as methanesulfonate, fluorosulfonate, and tosylate, etc.

While the designations

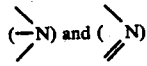

refer to virtually any tertiary aliphatic amine and aromatic amine moiety, respectively, the following moieties are preferred:
Pyridine
Methylnicotinate
Ethylnicotinate
Trimethylamine
Triethylamine
N-Benzoyloxymethyl
N-Pivaloyloxymethyl
Methylimidazole
1,4-Diazabicyclo[2.2.2.]octane
Nicotinamide
N-Ethylnicotinamide Finally, the term "naturally occurring bile acid" denotes any free or conjugated bile acid occurring in man such as cholic acid, deoxycholic acid, chenodeoxycholic acid, glycocholic acid, etc.

DETAILED DESCRIPTION OF THE INVENTION

While all the compounds encompassed within the above formula (I) satisfy the objectives of the present invention, nevertheless, certain compounds remain preferred as set out below:
(1) 1-α-(Benzoyloxymethyl)-3-carbamoyl-pyridinium chloride
(2) 1-(Benzoyloxybenzyl)-3-carbamoyl-pyridinium bromide
(3) 1-(Cinnamoyloxymethyl)-3-carbamoyl-pyridinium chloride
(4) 1-(α-Benzoyloxyethyl)-3-carbamoyl-pyridinium chloride
(5) 1-(α-Cinnamoyloxyethyl)-3-carbamoyl-pyridinium chloride
(6) 1-(Benzoyloxymethyl)-ethylnicotinate chloride
(7) 1-(Cinnamoyloxymethyl)-ethylnicotinate chloride
(8) 1-(α-Benzoyloxybenzyl)-ethylnicotinate chloride
(9) 1-(α-Cinnamoyloxybenzyl)-ethylnicotinate chloride
(10) Benzoyloxymethyl-triethylammonium chloride
(11) α-Benzoyloxybenzyl-triethylammonium bromide
(12) Cinnamoyloxymethyl-triethylammonium chloride
(13) α-Benzoyloxyethyl-triethylammonium chloride
(14) α-Cinnamoyloxyethyl-triethylammonium chloride
(15) ω-(Diethyl-benzoyloxymethyl-ammonium)-2,6-dimethylacetanilide chloride
(16) ω-(Diethyl-α-benzoyloxybenzyl-ammonium)-2,6-dimethylacetanilide chloride
(17) ω-(Diethyl-cinnamoyloxymethyl-ammonium)-2,6-dimethylacetanilide chloride
(18) ω-[Diethyl-(α-benzoyloxyethyl)-ammonium]-2,6-dimethylacetanilide chloride
(19) ω-[Diethyl-(α-cinnamoyloxyethyl)-ammonium]-2,6-dimethylacetanilide chloride
(20) N,N-dimethylglycine methyl ester-N-benzoyloxymethyl chloride
(21) N,N-diethylglycine ethyl ester-N-benzoyloxymethyl chloride
(22) ω-(Diethyl-pivaloyloxymethyl-ammonium)-2,6-dimethylacetanilide chloride
(23) N,N-dimethylglycine methyl ester-N-pivaloyloxymethyl chloride
(24) N,N-diethylglycine pyridine methanol ester-N-pivaloyloxymethyl chloride
(1) n-Octanoyloxymethylpyridinium chloride.
(2) n-Dodecanoyloxymethylpyridinium chloride.
(3) n-Tetradecanoyloxymethylpyridinium chloride.
(4) n-Hexadecanoyloxymethylpyridinium chloride.
(5) 1-n-Dodecanoyloxymethyl-3-methylimidazolium chloride.
(6) 1-n-Tetradecanoyloxymethyl-3-methylimidazolium chloride.
(7) 1-n-Hexadecanoyloxymethyl-3-methylimidazolium chloride.
(8) n-Dodecanoyloxymethyltriethylammonium chloride.
(9) 1-n-Dodecanoyloxymethyl-1,4-diazabicyclo [2.2.2.] octane chloride.
(10) 1-n-Dodecanoyloxymethyl-N-ethylnicotinamide chloride.
(11) n-Octanoyloxymethyl-3-methylimidazolium chloride or bromide.
(12) n-Octanoyloxymethyl-trimethylammonium chloride or bromide.
(13) n-Octanoyloxymethyl-nicotinamide chloride or bromide.

(14) 1-n-Octanoyloxymethyl-ethylnicotinate chloride or bromide.
(15) 1-n-Octanoyloxymethyl-methylnicotinate chloride or bromide.
(16) n-Octanoyloxymethyl-triethylammonium chloride or bromide.
(17) n-Decanoyloxymethyl-3-methylimidazolium chloride or bromide.
(18) 1-n-Decanoyloxymethyl-pyridinium chloride or bromide.
(19) n-Decanoyloxymethyl-trimethylammonium chloride or bromide.
(20) n-Decanoyloxymethyl-triethylammonium chloride or bromide.
(21) 1-n-Decanoyloxymethyl-nicotinamide chloride or bromide.
(22) 1-n-Decanoyloxymethyl-ethylnicotinate chloride or bromide.
(23) n-Dodecanoyloxymethyl-triethylammonium chloride or bromide.
(24) n-Tetradecanoyloxymethyl-trimethylammonium-chloride or bromide.
(25) n-Tetradecanoyloxymethyl-triethylammonium-chloride or bromide.
(26) 1-n-Tetradecanoyloxymethyl-nicotinamide chloride or bromide.
(27) 1-n-Tetradecanoyloxymethyl-ethylnicotinate chloride or bromide.
(28) 1-n-Tetradecanoyloxymethyl-methylnicotinate chloride or bromide.
(29) 1-n-Tetradecanoyloxymethyl-3-methylimidazolium chloride or bromide.
(30) n-Tetradecanoyloxymethyl-1,4-diazabicyclo [2.2.2.] octane chloride or bromide. (31) 1-[α-(n-Octanoyloxy)ethyl]-pyridinium chloride or bromide.
(32) 1-[α-(n-Octanoyloxy)ethyl]-3-methylimidazolium chloride or bromide.
(33) α-(n-Octanoyloxy)ethyl-trimethylammonium chloride or bromide.
(34) 1-[α-(n-Octanoyloxy)ethyl]-nicotinamide chloride or bromide.
(35) 1-[α-(n-Octanoyloxy)ethyl]-N-ethylnicotinamide chloride or bromide.
(36) 1-[α-(n-Octanoyloxy)ethyl]-ethylnicotinate chloride or bromide.
(37) 1-[α-(n-Decanoyloxy)ethyl]-pyridinium chloride or bromide.
(38) 1-[α-(n-Decanoyloxy)ethyl]-3-methylimidazolium chloride or bromide.
(39) α-(n-Decanoyloxy)ethyl-trimethylammonium chloride or bromide.
(40) α-(n-Decanoyloxy)ethyl-triethylammonium chloride or bromide.
(41) 1-[α-(n-Decanoyloxy)ethyl]-nicotinamide chloride or bromide.
(42) 1-[α-(n-Decanoyloxy)ethyl]-N-ethylnicotinamide chloride or bromide.
(43) 1-[α-(n-Decanoyloxy)ethyl]-ethylnicotinate chloride or bromide.
(44) 1-[α-(n-Decanoyloxy)ethyl]-1,4-diazabicyclo [2.2.2.] octane chloride or bromide.
(45) 1-[α-(n-Dodecanoyloxy)ethyl]-pyridinium chloride or bromide.
(46) α-(n-Dodecanoyloxy)ethyl-trimethylammonium chloride or bromide.
(47) α-(n-Dodecanoyloxy)ethyl-triethylammonium chloride or bromide.
(48) 1-[α-(n-Dodecanoyloxy)ethyl]-nicotinamide chloride or bromide.
(49) 1-[α-(n-Dodecanoyloxy)ethyl]-3-methylimidazolium chloride or bromide.
(50) 1-[α-(n-Dodecanoyloxy)ethyl]-N-ethylnicotinamide chloride or bromide.
(51) 1-[α-(n-Hexadecanoyloxy)ethyl]-pyridinium chloride or bromide.
(52) α-(n-Hexadecanoyloxy)ethyl-trimethylammonium chloride or bromide.
(53) α-(n-Hexadecanoyloxy)ethyl-triethylammonium chloride or bromide.
(54) 1-[α-(n-Hexadecanoyloxy)ethyl]-nicotinamide chloride or bromide.
(55) 1-[α-(n-Hexadecanoyloxy)ethyl]-3-methylimidazolium chloride or bromide.
(56) 1-[α-(n-Hexadecanoyloxy)ethyl]-N-ethylnicotinamide chloride or bromide.
(57) 1-[α-(n-Hexadecanoyloxy)ethyl]-ethylnicotinate chloride or bromide.
(58) 1-Oleyloxymethyl-pyridinium chloride or bromide.
(59) Oleyloxymethyl-trimethylammonium chloride or bromide.
(60) Oleyloxymethyl-trimethylammonium chloride or bromide.
(61) 1-Oleyloxymethyl-nicotinamide chloride or bromide.
(62) 1-Oleyloxymethyl-N-ethylnicotinamide chloride or bromide.
(63) 1-Oleyloxymethyl-ethylnicotinate chloride or bromide.
(64) 1-Oleyloxymethyl-3-methylimidazolium chloride or bromide.

A "most preferred" group of compounds from among all those described above is claimed hereinafter.

At this point, it should be strictly emphasized that when the substituent $R_1$ in formula (I) represents a $C_0$–$C_{22}$ straight or branched

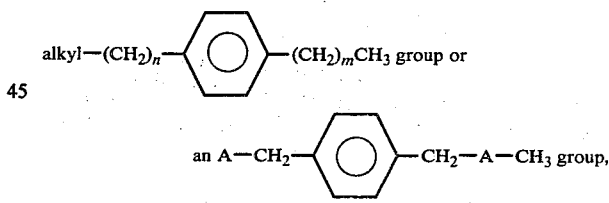

wherein A, n and m are defined above, any moiety known in the art which can be added to or substituted for the benzene ring in either one of the above long chain moieties for the purpose of improving their surface active agent properties may also be introduced. Typically, and without limitation, a pyridyl, a thiazolyl, an imidazolyl, or naphthyl function are illustrative.

The compounds of the present invention are suitably administered in oral dosage form, such as tablet or capsule, by combining the same in a therapeutically effective amount with any nontoxic oral pharmaceutically acceptable inert carrier material such as lactose, starch (pharmaceutical grade), dicalcium phosphate, calcium sulfate, kaolin, mannitol, and powdered sugar. Additionally, when required, suitable binders, lubricants, disintegrating agents and coloring agents can also be included in the formulation. Typical binders include, without limitation, starch, gelatine, sugars such as sucrose, molasses, and lactose, natural and synthetic gums such as acacia, sodium alginate, extract of Irish Moss, carboxymethylcellulose, methylcellulose, polyvinylpyrrolidone, polyethylene, glycol, ethylcellulose, and waxes. Typical lubricants include, without limitation, boric acid, sodium benzoate, sodium acetate, sodium chloride, leucine, and polyethylene glycol. Suitable disintegrators include, without limitation, starch, methylcellulose, agar, bentonite, cellulose, wood products, alginic acid, guar gum, citris pulp, carboxymethylcellulose and sodium lauryl sulfate. If desired, a nontoxic conventional pharmaceutically acceptable dye can also be incorporated into the dosage unit form, i.e., any of the standard approved FD&C dyes.

Any skilled artisan can prepare these oral dosage forms by simply referring to the oral dosage form preparatory procedure outlined in the text entitled "REMINGTON'S PHARMACEUTICAL SCIENCES" Fourteenth Edition (1970) pp. 1659 through 1698, inclusive.

While the therapeutic dosage range (that required to sufficiently bind bile acids) for the compounds of the present invention will vary with the size and needs of the subject, generally speaking, therapeusis on a daily basis will be achieved by administering 2 mg to 10 mg per Kg of body weight, about every 4 to 6 hours.

Without further elaboration, it is believed that one of ordinary skill in the art can, using the proceeding description, utilize the present invention to its fullest extent. Consequently, the following specific embodiments are, therefore, to be construed as merely illustrative, and not limitative of the remainder of the specification and claims in any way whatsoever.

EXAMPLE I

BILE ACID BINDING STUDIES

In order to demonstrate the binding of labile quaternary ammonium salts to bile acids, the electrode response of n-dodecanoyloxymethylpyridinium chloride (1), a representative labile quaternary salt, to sodium glycocholate (2) and sodium taurocholate (3) as a function of the solution pH was examined using the plastic ion selective cationic electrode (PISCE).

The results of these investigations are summarized in Tables 1 and 2.

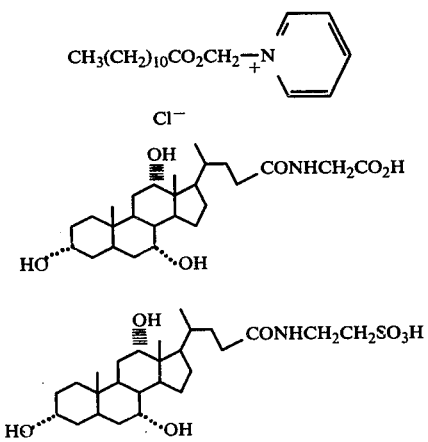

Table 1

ELECTRODE RESPONSE OF 1 BINDING TO 2 AS A FUNCTION OF THE SOLUTION pH

| [1] | [2] | Electrode Response (mV) | | | |
|---|---|---|---|---|---|
| | | pH 1[a] | pH 3[a] | pH 5 | pH 7 |
| $1.00 \times 10^{-4}$ | $1.00 \times 10^{-4}$ | — | — | +116 | +45 |
| $1.00 \times 10^{-4}$ | $1.75 \times 10^{-4}$ | — | — | +110 | +40 |
| $1.00 \times 10^{-4}$ | $2.50 \times 10^{-4}$ | — | — | +109 | +39 |
| $1.00 \times 10^{-4}$ | $3.75 \times 10^{-4}$ | — | — | +108 | +38 |
| $1.00 \times 10^{-4}$ | $5.00 \times 10^{-4}$ | — | — | +107 | +38 |
| $1.00 \times 10^{-4}$ | $6.25 \times 10^{-4}$ | — | — | +106 | +37 |
| $1.00 \times 10^{-4}$ | $7.50 \times 10^{-4}$ | — | — | +106 | +37 |
| $1.00 \times 10^{-4}$ | $8.75 \times 10^{-4}$ | — | — | +106 | +36 |
| $1.00 \times 10^{-4}$ | $1.00 \times 10^{-3}$ | — | — | +105 | +36 |
| $1.00 \times 10^{-4}$ | $2.50 \times 10^{-3}$ | — | — | +91 | +27 |
| $1.00 \times 10^{-4}$ | $5.00 \times 10^{-3}$ | — | — | +62 | 0 |
| $1.00 \times 10^{-4}$ | $7.50 \times 10^{-3}$ | — | — | +34 | −28 |
| $1.00 \times 10^{-4}$ | $1.00 \times 10^{-2}$ | — | — | +9 | −53 |
| $1.00 \times 10^{-4}$ | — | — | — | +114 | +35 |
| — | — | −126 | −130 | −143 | −123 |
| — | $2.00 \times 10^{-4}$ | — | — | −121 | −76 |
| — | $1.00 \times 10^{-3}$ | — | — | −130 | −96 |
| — | $1.00 \times 10^{-2}$ | — | — | −157 | −171 |

[a] The limited solubility of 2 in pH 1 and pH 3 solutions inhibited an accurate determination of the binding properties of 1 under these conditions.

Table 2

Electrode Response Of 1 Binding To 3 As A Function Solution pH

| [1] | [2] | Electrode Response (mV) | | | |
|---|---|---|---|---|---|
| | | pH 1 | pH 3 | pH 5 | pH 7 |
| $1.00 \times 10^{-4}$ | $1.00 \times 10^{-4}$ | +85 | +112 | +105 | +53 |
| $1.00 \times 10^{-4}$ | $1.75 \times 10^{-4}$ | +85 | +93 | — | +51 |
| $1.00 \times 10^{-4}$ | $2.50 \times 10^{-4}$ | +84 | +91 | — | +50 |
| $1.00 \times 10^{-4}$ | $3.75 \times 10^{-4}$ | +83 | +89 | — | +48 |
| $1.00 \times 10^{-4}$ | $5.00 \times 10^{-4}$ | +82 | +88 | +103 | +49 |
| $1.00 \times 10^{-4}$ | $6.25 \times 10^{-4}$ | +81 | +86 | — | +48 |
| $1.00 \times 10^{-4}$ | $7.50 \times 10^{-4}$ | +82 | +86 | — | +47 |
| $1.00 \times 10^{-4}$ | $8.75 \times 10^{-4}$ | +81 | +85 | — | +47 |
| $1.00 \times 10^{-4}$ | $1.00 \times 10^{-3}$ | +81 | +84 | +101 | +47 |
| $1.00 \times 10^{-4}$ | $2.50 \times 10^{-3}$ | +72 | +69 | +86 | +33 |
| $1.00 \times 10^{-4}$ | $5.00 \times 10^{-3}$ | +44 | +35 | +59 | +4 |
| $1.00 \times 10^{-4}$ | $7.50 \times 10^{-3}$ | +19 | +10 | +34 | −21 |
| $1.00 \times 10^{-4}$ | $1.00 \times 10^{-2}$ | −2 | −11 | +11 | −42 |
| $1.00 \times 10^{-4}$ | — | +82 | +99 | +100 | +48 |
| — | — | −126 | −130 | −143 | −123 |
| — | $2.00 \times 10^{-4}$ | −34 | −33 | +4 | −58 |
| — | $1.00 \times 10^{-3}$ | −70 | −74 | −10 | −108 |
| — | $1.00 \times 10^{-2}$ | −123 | −135 | −83 | −180 |

Qualitatively, the decrease in the electrode response to 1 as the concentration of 2 and/or 3 is increased is indicative of the binding of the labile quaternary salt to the conjugated bile acid.

From the foregoing description, one of ordinary skill in the art can easily ascertain the essential characteristics of this invention, and without departing from the spirit and scope thereof, can make various changes and/or modifications to the invention for adapting it to various usages and conditions. Accordingly, such changes and modifications are properly, equitably and intended to be, within the full range of equivalence of the following claims.

What I claim is:

1. A method for substantially binding free and conjugated bile acids present in the stomach of a warm-blooded animal characterized as being ulcer-prone which comprises orally administering to the stomach of such animal, a therapeutically effective gastric bile acid binding amount of a compound having the formula:

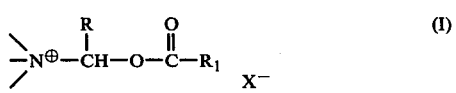

wherein

represents a lower alkyl quaternary ammonium group; wherein R represents a member selected from the group consisting of a hydrogen atom, a $C_1$-$C_{20}$ open chain or cyclo alkyl group, a $C_1$-$C_{20}$ alkoxyalkyl group, a $C_1$-$C_{20}$ alkanoyloxyalkyl group, a $C_1$-$C_{20}$ haloalkyl group, a $C_1$-$C_{20}$ carboxyalkyl group, a phenyl group, a naphthyl group, and a substituted phenyl or naphthyl group, whose substituents are selected from the group consisting of a halogen atom, an O—$C_1$-$C_4$ alkyl group, an O—$C_1$-$C_8$ alkanoyl group, a nitro group, a carboxyl group, an a carboethoxy group; wherein $R_1$, which may be the same or different, represents any member defined by R above with the proviso that R cannot be a hydrogen atom, a

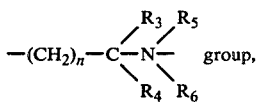

wherein $R_3$, $R_4$, $R_5$ and $R_6$ are each selected from the group consisting of a hydrogen atom, a methyl group or an ethyl group, a $C_1$-$C_{22}$ straight or branched

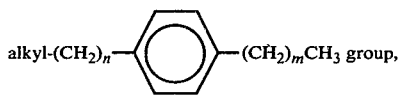

wherein n in each occurrence and m represent an integer of from 0 to 22, an

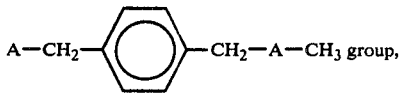

wherein A represents a $C_1$-$C_{22}$ straight or branched alkyl group as above or a —$(CH_2CH_2O)_p$ group, wherein the p represents an integer of from 0 to 22, and the residue of any naturally occurring bile acid selected from the group consisting of cholic acid, deoxycholic acid, glycocholic acid and chenodeoxycholic acid; and wherein X represents a halogen atom, a methanesulfonate group, a fluorosulfonate group and a tosylate group.

2. The method of claim 1, wherein said compound is: n-Dodecanoyloxymethyltriethylammonium chloride.

3. The method of claim 1, wherein said compound is: n-Octanoyloxymethyl-trimethylammonium chloride or bromide.

4. The method of claim 1, wherein said compound is: n-Octanoyloxymethyl-triethylammonium chloride or bromide.

5. The method of claim 1, wherein said compound is: n-Dodecanoyloxymethyl-triethylammonium chloride or bromide.

6. The method of claim 1, wherein said compound is: n-Tetradecanoyloxymethyl-trimethylammonium-chloride or bromide.

7. The method of claim 1, wherein said compound is: n-Tetradecanoyloxymethyl-triethylammonium-chloride or bromide.

8. The method of claim 1, wherein said compound is: α-(n-Decanoyloxy)ethyl-trimethylammonium chloride or bromide.

9. The method of claim 1, wherein said compound is: α-(n-Dodecanoyloxy)ethyl-trimethylammonium chloride or bromide.

10. The method of claim 1, wherein said compound is: α-(n-Hexadecanoyloxy)ethyl-trimethylammonium chloride or bromide.

11. The method of claim 1, wherein said compound is: Oleyloxymethyl-trimethylammonium chloride or bromide.

12. The method of claim 1, wherein said compound is administered in combination with an orally nontoxic pharmaceutically acceptable inert carrier material.

* * * * *